United States Patent
Rampf et al.

(10) Patent No.: US 9,688,567 B2
(45) Date of Patent: Jun. 27, 2017

(54) LITHIUM DISILICATE-APATITE GLASS CERAMIC WITH TRANSITION METAL OXIDE

(71) Applicant: Ivoclar Vivadent AG, Schaan (LI)

(72) Inventors: Markus Rampf, Lachen (CH); Christian Ritzberger, Grabs (CH); Marcel Schweiger, Chur (CH); Wolfram Höland, Schaan (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/023,864

(22) PCT Filed: Nov. 5, 2014

(86) PCT No.: PCT/EP2014/073790
§ 371 (c)(1),
(2) Date: Mar. 22, 2016

(87) PCT Pub. No.: WO2015/067643
PCT Pub. Date: May 14, 2015

(65) Prior Publication Data
US 2016/0236971 A1 Aug. 18, 2016

(30) Foreign Application Priority Data
Nov. 5, 2013 (EP) ..................... 13191689

(51) Int. Cl.
| C03C 10/12 | (2006.01) |
| C03C 10/00 | (2006.01) |
| C03C 3/112 | (2006.01) |
| C03C 4/00 | (2006.01) |
| C03C 10/16 | (2006.01) |
| A61K 6/02 | (2006.01) |
| A61K 6/027 | (2006.01) |
| A61K 6/033 | (2006.01) |
| C03B 32/02 | (2006.01) |
| C03C 1/00 | (2006.01) |

(52) U.S. Cl.
CPC .......... C03C 10/0027 (2013.01); A61K 6/024 (2013.01); A61K 6/025 (2013.01); A61K 6/0255 (2013.01); A61K 6/0273 (2013.01); A61K 6/033 (2013.01); C03B 32/02 (2013.01); C03C 1/00 (2013.01); C03C 3/112 (2013.01); C03C 4/0021 (2013.01); C03C 10/16 (2013.01)

(58) Field of Classification Search
CPC ............ C03C 10/0009; C03C 10/0018; C03C 10/0027; C03C 10/0036
USPC .............................. 501/5, 6, 7, 8, 9
See application file for complete search history.

(56) References Cited

U.S. PATENT DOCUMENTS

| 6,455,451 B1 | 9/2002 | Brodkin et al. |
| 6,517,623 B1 * | 2/2003 | Brodkin .................. C03B 19/06 106/35 |
| 2015/0087493 A1 | 3/2015 | Ritzberger et al. |
| 2016/0075593 A1 | 3/2016 | Ritzberger et al. |

FOREIGN PATENT DOCUMENTS

| EP | 231773 A1 | 8/1987 |
| EP | 1505041 A1 | 2/2005 |
| WO | 2013164256 A1 | 11/2013 |

OTHER PUBLICATIONS

Holand et al. Studies of crystal phase formations in high-strength lithium disilicate glass—ceramics. Journal of Non-Crystalline Solids 352 (2006) 4041-4050.*
Palou et al. Mechanism and kinetics of glass-ceramics formation in the LiO2—SiO2—CaO—P2O5-CaF2 system. Cent. Eur. J. Chem. • 7(2) • 2009 • 228-233.*
Kasuga et al. Preparation of a Calcium Titanium Phosphate Glass—Ceramic with Improved Chemical Durability. J. Am. Ceram. Soc., 92 [8] 1709-1712 (2009).*
Palou, M., et al., "Mechanism and kinetics of glass-ceramics formation in the LiO2—SiO2—Ca0—P205—CaF2 system," Cent. Eur. J. Chem., 2009, pp. 228-233, vol. 7, Issue 2.
Mojumdar, S.C., et al., "Fluoroapatite—material for medicine growth, morphology and thermoanalytical properties," Journal of Thermal Analysis and Calorimetry, Sep. 2004, pp. 73-82, vol. 78, Issue 1.
International Preliminary Report on Patentability of PCT/EP2014/073790, May 10, 2016, 17 pages.
Martin Palou, "Mechanism and kinetics of glass-ceramics formation in the Li20—SiO2—CaO—P205—CaF2 System," Central European Journal of Chemistry, Central European Science Journals, PL; US; NL; DE, vol. 7, No. 2, Jan. 1, 2009, pp. 228-233, XP002682499, ISSN: 1644-3624.

* cited by examiner

*Primary Examiner* — Noah Wiese
(74) *Attorney, Agent, or Firm* — Ann M. Knab; Thad McMurray

(57) ABSTRACT

Lithium disilicate-apatite glass ceramics comprising transition metal oxide are described which are characterized by a high chemical stability, and the translucence of which can be adjusted as desired, and which can therefore be used in particular as restoration material in dentistry.

41 Claims, No Drawings

LITHIUM DISILICATE-APATITE GLASS CERAMIC WITH TRANSITION METAL OXIDE

CROSS-REFERENCE TO RELATED APPLICATIONS

This application is a National Stage application of International patent application PCT/EP2014/073790 filed on Nov. 5, 2014, which claims priority to European patent application No. 13191689.2 filed on Nov. 5, 2013, the disclosures of which are incorporated herein by reference in their entirety.

The invention relates to lithium disilicate-apatite glass ceramic which comprises transition metal oxide and is suitable in particular for use in dentistry, preferably for the preparation of dental restorations, as well as precursors to its preparation.

Glass ceramics with a lithium disilicate and an apatite crystal phase are known from the state of the art.

In Cent. Eur. J. Chem, 7(2), 228-233 (2009), M. Palou et al. report on the crystallization of a mixture of pure lithium disilicate glass and fluoroapatite glass. The glass ceramic produced has a high amount of 14 wt.-% of $P_2O_5$ and displays bioactivity during in-vitro tests in simulated body fluid.

In the Journal of Thermal Analysis and calorimetry 78(1), 73-(2004), S. C. Mojumdar et al. describe studies on the crystallization of glasses from the $Li_2O$—$CaO$—$CaF_2$—$P_2O_5$—$SiO_2$ system with different amounts of $P_2O_5$. After crystallization of a glass with an amount of 15 wt.-% of $P_2O_5$, fluoroapatite was detected in addition to a lithium disilicate crystal phase by means of X-ray diffraction.

However, the lithium silicate glass ceramics with apatite crystal phase known from the state of the art are bioactive products and not chemically resistant materials which are suitable for restorative dentistry. In body fluids or simulated body fluids, bioactive products form apatite crystals on the surface in order, e.g. in the case of an endoprosthetic implant, to produce a solid bond with the bone.

Therefore, the known glass ceramics have the serious disadvantage that they do not possess the chemical stability required for a dental material which comes into contact with a wide variety of fluids in the oral cavity.

Therefore the object of the invention is to make available a lithium disilicate-apatite glass ceramic which has a very good chemical stability and can thus be used as restorative dental material. The glass ceramic shall also be capable of being readily processed into dental restorations, and the restorations produced from it shall also have very good mechanical and optical properties in addition to a very good chemical stability.

This object is achieved by the lithium disilicate-apatite glass ceramic according to claims 1 to 15 and 19. Also a subject of the invention are the starting glass according to claim 16, 17 or 19, the lithium metasilicate glass ceramic according to claim 18 or 19, the process according to claims 20 and 21 as well as the use according to claims 22 and 23.

The lithium disilicate-apatite glass ceramic according to the invention is characterized in that it comprises lithium disilicate as main crystal phase and apatite as further crystal phase, and it comprises divalent oxide selected from the group of CaO, SrO and mixtures thereof and transition metal oxide selected from the group of oxides of the transition metals with an atomic number from 39 to 79 and mixtures thereof, wherein the molar ratio of divalent oxide to transition metal oxide is in the range of from 1.0 to 20.0, in particular 1.0 to 17.0 and preferably 1.5 to 16.5.

The term "main crystal phase" refers to the crystal phase which has the highest proportion by volume compared with other crystal phases.

Surprisingly, the lithium disilicate-apatite glass ceramic according to the invention is characterized by a very high chemical stability. To determine the chemical stability, the glass ceramic was tested according to ISO standard 6872 (2008) by determining the mass loss during storage in aqueous acetic acid. The lithium disilicate-apatite glass ceramic according to the invention displayed in particular a mass loss of less than 100 $\mu g/cm^2$, preferably less than 90 and particularly preferably less than 80 $\mu g/cm^2$ and quite particularly preferably less than 50 $\mu g/cm^2$.

Furthermore, within the range given for the molar ratio of divalent oxide to transition metal oxide, it is surprisingly possible to adjust the translucence of the lithium disilicate-apatite glass ceramic according to the invention in a controlled manner. While incorporating the transition metal oxide leads to an increase in the translucence, the crystallization of apatite decreases the translucence of the glass ceramic according to the invention. The translucence can thus be adjusted as desired by these two opposing effects. This is an exceptional advantage specifically for dental materials as, depending on their intended use, a different amount of light transmission is desired. The transition metal oxides present in the glass ceramic are components that are sterically relatively large, with the result that their incorporation should lead to a significant change in the structure. It is thus surprising that, despite the incorporation of transition metal oxide, the simultaneous crystallization of both lithium disilicate and apatite can be accomplished.

The lithium disilicate-apatite glass ceramic according to the invention preferably comprises 52.0 to 75.0, in particular 54.0 to 73.0 wt.-% $SiO_2$.

It is also preferred that the lithium-disilicate apatite glass ceramic comprises 10.0 to 20.0, in particular 12.0 to 20.0 wt.-% $Li_2O$.

The molar ratio of $SiO_2$ to $Li_2O$ in the glass ceramic preferably lies in the range of from 1.5 to 3.0.

Furthermore, a lithium disilicate-apatite glass ceramic is preferred which comprises 4.0 to 8.0 wt.-% $P_2O_5$.

The glass ceramic according to the invention comprises in particular 2.0 to 9.0, preferably 3.0 to 8.0 wt.-% of the divalent oxide or mixtures thereof.

In a further preferred embodiment, the glass ceramic according to the invention comprises 2.5 to 8.5, in particular 3.0 to 8.0 wt.-% CaO and/or 1.0 to 6.5, in particular 1.0 to 6.0 wt.-% SrO.

A lithium disilicate-apatite glass ceramic which comprises 0.1 to 1.5, in particular 0.3 to 1.0 wt.-% F is also preferred.

The formation of fluoroapatite is possible by using fluorine. It is particularly preferred that the glass ceramic according to the invention comprises fluoroapatite as apatite. Depending on the cation, the fluoroapatite is present in particular as Ca-fluoroapatite, Sr-fluoroapatite or mixed Ca/Sr-fluoroapatite.

A glass ceramic according to the invention is preferred in which the apatite crystal phase makes up 0.5 to 10, in particular 1 to 10 and preferably 2 to 8 wt.-% of the glass ceramic and/or the apatite crystals have an average size of from 5 to 500, in particular 10 to 300 and preferably 20 to 200 nm.

The average size of the crystals was calculated as L from the X-ray diffraction diagrams using the Scherrer equation:

$$\Delta(2\theta) = \frac{K\lambda}{L\cos\theta}$$

K: Scherrer shape factor
λ: wavelength
θ: diffraction angle
L: Crystallite extension perpendicular to the lattice plane (average crystallite size)

JCPDS file 01-074-4390 was used as reference pattern for the apatite crystals.

In a preferred embodiment, the glass ceramic also comprises 0 to 4.0, in particular 1.0 to 4.0 and preferably 1.5 to 4.0 wt.-% $Al_2O_3$.

The glass ceramic according to the invention usually comprises 0.5 to 8.5, in particular 1.0 to 8.0 and preferably 2.0 to 7.5 wt.-% of the transition metal oxide or mixtures thereof.

The transition metal oxide present in the glass ceramic is preferably selected from the group of $La_2O_3$, $Y_2O_3$, $Er_2O_3$, $ZrO_2$, $CeO_2$, $Tb_4O_7$, $V_2O_5$, $Ta_2O_5$, $Nb_2O_5$ and mixtures thereof.

A glass ceramic according to the invention is further preferred in which the transition metal oxide is present
according to the formula $Me_2O_3$ in an amount of from 0 to 5.0, in particular 2.5 to 4.0 wt.-%,
according to the formula $MeO_2$ in an amount of from 0 to 6.5, in particular 1.0 to 6.0 wt.-%,
according to the formula $Me_4O_7$ in an amount of from 0 to 1.0, in particular 0.4 to 1.0 wt.-% and/or
according to the formula $Me_2O_5$ in an amount of from 0 to 5.0, in particular 0.1 to 4.0 wt.-%.

In the given formulae, "Me" stands for the respective transition metal with an atomic number from 39 to 79.

The lithium disilicate-apatite glass ceramic according to the invention usually comprises monovalent oxide selected from the group of $Na_2O$, $K_2O$, $Rb_2O$, $Cs_2O$ and mixtures thereof in an amount of from 0 to 12.0, in particular 2.0 to 12.0 and preferably 3.0 to 11.5 wt.-%.

Furthermore, a lithium disilicate-apatite glass ceramic is preferred which comprises at least one and in particular all of the following components:

| Component | wt.-% |
|---|---|
| $SiO_2$ | 52.0 to 75.0 |
| $Li_2O$ | 10.0 to 20.0 |
| $P_2O_5$ | 4.0 to 8.0, |
| divalent oxide | 2.0 to 9.0 |
| F | 0.1 to 1.5, |
| $Al_2O_3$ | 0 to 4.0, |
| transition metal oxide | 0.5 to 8.5, |
| monovalent oxide | 0 to 12.0. |

The lithium disilicate-apatite glass ceramic according to the invention can also comprise further additional components which in particular are selected from colorants and fluorescent agents. Examples of colorants and fluorescent agents are oxides of d- and f-elements.

In a further preferred embodiment the lithium disilicate apatite glass ceramic according to the invention comprises more than 10 vol.-%, preferably more than 20 vol.-% and particularly preferably more than 30 vol.-% lithium disilicate crystals, relative to the total glass ceramic.

The glass ceramic according to the invention with lithium disilicate as main crystal phase is characterized by particularly good mechanical properties, and it can be formed e.g. by heat treatment of a corresponding starting glass or a corresponding starting glass with nuclei or a corresponding lithium metasilicate glass ceramic.

It has further been shown that the lithium disilicate-apatite glass ceramic according to the invention has an excellent chemical stability and also has very good mechanical and optical properties. Furthermore, it is possible to adjust its translucence in a controlled manner by the transition metal oxide as well as the apatite crystal phase by exploiting on the one hand the translucence-increasing effect of the transition metal oxide and on the other hand the translucence-reducing effect of the apatite. Its linear coefficient of thermal expansion can also be adjusted over a broad range.

It is thus superior to the known lithium disilicate-apatite glass ceramics. The combination of its properties even allows it to be used as dental material and in particular as material for the preparation of dental restorations.

The lithium disilicate-apatite glass ceramic according to the invention has in particular a fracture toughness, measured as $K_{IC}$ value, of at least about 1.5 MPa·m$^{0.5}$ and in particular at least about 1.8 MPa·m$^{0.5}$. This value was determined using the Vickers method and calculated using Niihara's equation. Furthermore, it has a high biaxial breaking strength of in particular at least about 200 and preferably at least about 300 MPa. The biaxial breaking strength was determined according to ISO 6872 (2008).

The invention also relates to various precursors with the corresponding composition from which the lithium disilicate-apatite glass ceramic according to the invention can be prepared by heat treatment. These precursors are a corresponding starting glass, a corresponding starting glass with nuclei and a corresponding lithium metasilicate glass ceramic.

The invention, therefore, also relates to a starting glass which comprises the components of the lithium disilicate-apatite glass ceramic according to the invention.

The starting glass according to the invention thus comprises divalent oxide selected from the group of CaO, SrO and mixtures thereof and transition metal oxide selected from the group of oxides of the transition metals with an atomic number from 39 to 79 and mixtures thereof, wherein the molar ratio of divalent oxide to transition metal oxide is in the range of from 1.0 to 20.0, in particular 1.0 to 17.0 and preferably 1.5 to 16.5.

The starting glass according to the invention moreover also comprises in particular suitable amounts of further components required to form the glass ceramic according to the invention with lithium disilicate as main crystal phase and apatite as further crystal phase. Preferably, it comprises $SiO_2$ and $Li_2O$ in amounts which make the formation of lithium disilicate possible. Furthermore, the starting glass can also comprise still further components such as are given above for the lithium disilicate-apatite glass ceramic according to the invention. All those embodiments which are given as preferred for the components of the lithium disilicate-apatite glass ceramic according to the invention are also preferred for the components of the starting glass.

The invention also relates to a starting glass which comprises nuclei for the crystallization of lithium metasilicate, lithium disilicate and/or apatite.

Furthermore, the invention relates to a lithium metasilicate glass ceramic which comprises lithium metasilicate in particular as main crystal phase and the components of the lithium disilicate-apatite glass ceramic according to the invention.

The lithium metasilicate glass ceramic according to the invention thus comprises divalent oxide selected from the group of CaO, SrO and mixtures thereof and transition metal oxide selected from the group of oxides of the transition metals with an atomic number from 39 to 79 and mixtures thereof, wherein the molar ratio of divalent oxide to transition metal oxide is in the range of from 1.0 to 20.0, in particular 1.0 to 17.0 and preferably 1.5 to 16.5.

The lithium metasilicate glass ceramic according to the invention moreover also comprises in particular suitable amounts of further components required to form the glass ceramic according to the invention with lithium disilicate as main crystal phase and apatite as further crystal phase. Furthermore, the lithium metasilicate glass ceramic can also comprise still further components, such as are given above for the lithium disilicate-apatite glass ceramic according to the invention. All those embodiments which are given as preferred for the components of the lithium disilicate-apatite glass ceramic according to the invention are also preferred for the components of the lithium metasilicate glass ceramic.

In a further embodiment, the lithium metasilicate glass ceramic according to the invention also comprises apatite and/or lithium disilicate as further crystal phase(s).

By heat treating the starting glass, the further precursors starting glass with nuclei and lithium metasilicate glass ceramic can firstly be produced. The lithium disilicate-apatite glass ceramic according to the invention can then be produced by heat treating one of these two further precursors. It is preferred to form the lithium disilicate-apatite glass ceramic according to the invention directly by heat treating the starting glass with nuclei.

It is preferred to subject the starting glass to a heat treatment at a temperature of from 450 to 600° C., in particular 450 to 550° C., for a period of from 5 to 120 min, in particular to 60 min, in order to produce the starting glass with nuclei for the crystallization of lithium metasilicate, lithium disilicate and/or apatite.

It is further preferred to subject the starting glass with nuclei to a heat treatment at a temperature of more than 600° C. for a period of from 5 to 120 min, in particular 10 to 60 min, in order to prepare the lithium metasilicate glass ceramic or the lithium disilicate-apatite glass ceramic. To prepare the lithium disilicate-apatite glass ceramic, the heat treatment of the starting glass with nuclei takes place particularly preferably at 700 to 1000° C., in particular 750 to 950° C., for a period of from 5 to 120 min, in particular 10 to 60 min.

The invention also relates to a process for the preparation of the lithium disilicate-apatite glass ceramic according to the invention in which the starting glass, the starting glass with nuclei or the lithium metasilicate glass ceramic is subjected to at least one heat treatment in the range of from 450 to 1000° C.

The at least one heat treatment carried out in the process according to the invention can also take place during a hot pressing or sintering-on of the starting glass according to the invention, of the starting glass according to the invention with nuclei or of the lithium metasilicate glass ceramic according to the invention.

In a preferred embodiment the process according to the invention comprises
(a) the heat treatment of the starting glass at a temperature of from 450 to 600° C. in order to form the starting glass with nuclei, and
(b) the heat treatment of the starting glass with nuclei at a temperature of from 700 to 1000° C. in order to form the lithium disilicate-apatite glass ceramic.

The duration of the heat treatments carried out in (a) and (b) is in particular 5 to 120 min and preferably 10 to 60 min.

To prepare the starting glass, the procedure is in particular that a mixture of suitable starting materials, such as carbonates, oxides, phosphates and fluorides, is melted at temperatures of in particular from 1300 to 1600° C. for 2 to 10 h. To achieve a particularly high homogeneity, the obtained glass melt is poured into water in order to form a glass granulate, and the obtained granulate is then melted again.

The melt can then be poured into moulds to produce blanks of the starting glass, so-called solid glass blanks or monolithic blanks.

It is also possible to put the melt into water again in order to prepare a granulate. This granulate can be pressed, after grinding and optionally addition of further components, such as colorants and fluorescent agents, to form a blank, a so-called powder green compact.

Finally, the starting glass can also be processed to form a powder after granulation.

The starting glass, e.g. in the form of a solid glass blank, a powder green compact or in the form of a powder, is then subjected to at least one heat treatment. It is preferred that a first heat treatment is initially carried out to prepare a starting glass according to the invention with nuclei which are suitable for forming lithium metasilicate, lithium disilicate and/or apatite crystals. The glass with nuclei is then usually subjected to at least one further temperature treatment at a higher temperature in order to effect crystallization of lithium metasilicate, lithium disilicate and/or apatite.

The further heat treatment for crystallizing lithium metasilicate takes place in particular at a temperature of at least 600° C. For crystallizing lithium disilicate, the further heat treatment takes place in particular at a temperature of at least 700° C. For crystallizing apatite, the further heat treatment takes place in particular at a temperature of at least 750° C.

The glass ceramics according to the invention and the glasses according to the invention are present in particular in the form of powders, granulates or blanks in any form or size, e.g. monolithic blanks, such as platelets, cuboids or cylinders, or powder green compacts, in unsintered, partly sintered or densely-sintered form. They can easily be further processed in these shapes. They can, however, also be present in the form of dental restorations, such as bridges, inlays, onlays, crowns, veneers, facets or abutments.

Dental restorations, such as bridges, inlays, onlays, crowns, veneers, facets or abutments, can be prepared from the glass ceramics according to the invention and the glasses according to the invention. The invention therefore also relates to their use for the preparation of dental restorations. It is preferred that the glass ceramic or the glass is given, by pressing or machining, the shape of the desired dental restoration.

The pressing usually takes place under increased pressure and increased temperature. It is preferred that the pressing is carried out at a temperature of from 700 to 1200° C. It is further preferred to carry out the pressing at a pressure of from 2 to 10 bar. During pressing, the desired shape change is achieved by viscous flow of the material used. The starting glass according to the invention and in particular the starting glass according to the invention with nuclei, the lithium metasilicate glass ceramic according to the invention and the lithium disilicate-apatite glass ceramic according to the invention can be used for the pressing. The glasses and glass ceramics according to the invention can be used in particular in the form of blanks in any form or size, e.g. solid blanks or powder green compacts, e.g. in unsintered, partly sintered or densely-sintered form.

The machining usually takes place by material removal processes and in particular by milling and/or grinding. It is particularly preferred that the machining is carried out as part of a CAD/CAM process. The starting glass according to the invention, the starting glass according to the invention with nuclei, the lithium metasilicate glass ceramic according to the invention and the lithium disilicate-apatite glass ceramic according to the invention can be used for the machining. The glasses and glass ceramics according to the invention can be used in particular in the form of blanks, e.g. solid blanks or powder green compacts, e.g. in unsintered, partly sintered or densely-sintered form. Preferably the lithium metasilicate glass ceramic according to the invention or the lithium disilicate-apatite glass ceramic according to the invention is used for the machining. The lithium disilicate-apatite glass ceramic can also be used in a not yet fully crystallized form which was produced by heat treatment at a lower temperature. This has the advantage that an easier machining and thus the use of simpler equipment for the machining is possible. After the machining of such a partly crystallized material, the latter is usually subjected to a heat treatment at a higher temperature and in particular 700 to 1000° C. and preferably 750 to 950° C. in order to effect further crystallization of lithium disilicate and apatite.

In general, after the preparation of the dental restoration shaped as desired, e.g. by pressing or machining, the latter in particular is heat-treated again in order to convert the precursors used, such as starting glass, starting glass with nuclei or lithium metasilicate glass ceramic, into lithium disilicate-apatite glass ceramic or increase the crystallization of lithium disilicate and/or apatite or reduce the porosity, e.g. of a porous powder green compact used.

However, the glass ceramics according to the invention and the glasses according to the invention are also suitable as coating material of e.g. ceramics, such as $ZrO_2$ ceramics, and glass ceramics. The invention is therefore also directed towards the use of the glasses according to the invention or the glass ceramics according to the invention for coating in particular ceramics and glass ceramics. It proves to be very beneficial that the glass ceramics according to the invention have a linear coefficient of thermal expansion which lies in a broad range of in particular from 8.0 to $13.5 \times 10^{-6} K^{-1}$ (measured in the range of from 100 to 500° C.). A glass ceramic according to the invention with the desired coefficient of expansion is thus available for a wide variety of applications.

The invention also relates to a process for coating ceramics and glass ceramics, in which glass ceramics according to the invention or glasses according to the invention are applied to the ceramic or glass ceramic and are subjected to increased temperature.

This can take place in particular by sintering-on and preferably by pressing-on. With sintering-on, the glass ceramic or the glass is applied to the material to be coated, such as ceramic or glass ceramic, in the usual way, e.g. as powder, and then sintered at increased temperature. With the preferred pressing-on, glass ceramic according to the invention or glass according to the invention is pressed on, e.g. in the form of powder green compacts or monolithic blanks, at an increased temperature of e.g. from 700 to 1200° C., and applying pressure, e.g. 2 to 10 bar. The methods described in EP 231 773 and the press furnace disclosed there can be used in particular for this. A suitable furnace is e.g. the Programat EP 5000 from Ivoclar Vivadent AG, Liechtenstein.

It is preferred that, after conclusion of the coating process, the glass ceramic according to the invention is present with lithium disilicate as main crystal phase and apatite as further crystal phase, as such a glass ceramic has particularly good properties.

Because of the above-described properties of the glass ceramics according to the invention and the glasses according to the invention, these are suitable in particular for use in dentistry. A subject of the invention is therefore also the use of the glass ceramics according to the invention or the glasses according to the invention as dental material and in particular for the preparation of dental restorations or as a coating material for dental restorations, such as crowns, bridges and abutments.

The invention is described in further detail below with reference to non-limiting examples.

EXAMPLES

Examples 1 to 20—Composition and Crystal Phases

A total of 20 glasses and glass ceramics according to the invention with the composition given in the table below were prepared by melting corresponding starting glasses followed by heat treatment for controlled nucleation and crystallization.

The $T_g$ values of the glasses as well as the heat treatments used for controlled nucleation and controlled crystallization are also given in the table. The following meanings apply
$T_N$ and $t_N$ temperature and time used for nucleation
$T_{K1}$ and $t_{K1}$ temperature and time used for a 1st crystallization
$T_{K2}$ and $t_{K2}$ temperature and time used for a 2nd crystallization For this, the starting glasses in batches of 100 to 200 g were first melted from customary raw materials at 1400 to 1500° C., wherein the melting was very easily possible without formation of bubbles or streaks. By pouring the starting glasses into water, glass frits were produced which were then melted a second time at 1450 to 1550° C. for 1 to 3 h for homogenization.

A heat treatment of the starting glasses at a temperature of from 460 to 540° C. led to the formation of lithium silicate glasses with nuclei.

As a result of at least one further heat treatment, these nuclei-containing glasses crystallized to form glass ceramics with lithium metasilicate as main crystal phase or glass ceramics with lithium disilicate as main crystal phase and apatite as further crystal phase, as was established by X-ray diffraction tests. The apatite was present as Ca-fluoroapatite, Sr-fluoroapatite or Ca/Sr-fluoroapatite.

In Examples 1 to 4, 7, 9, 10 and 15, a first further heat treatment $T_{K1}$ of the nuclei-containing starting glasses led to glass ceramics with lithium metasilicate as main crystal phase and the obtained lithium metasilicate glass ceramics were converted into glass ceramics with lithium disilicate as main crystal phase and apatite as further crystal phase by a second further heat treatment $T_{K2}$.

In Examples 13, 14, 16, 17, 19 and 20, the nuclei-containing starting glasses were converted into glass ceramics with lithium disilicate as main crystal phase and apatite as further crystal phase by only one further heat treatment, and in the case of Example 18 into a glass ceramic with lithium metasilicate as main crystal phase and apatite as further crystal phase.

In Examples 8, 11 and 12, glass ceramics with lithium metasilicate as main crystal phase were also present after the second further heat treatment.

Finally, Examples 5 and 6 show the production of glass ceramics with lithium disilicate as main crystal phase even after the first further heat treatment and the further crystallization thereof by a second further heat treatment.

The examples thus collectively show how different glass ceramics according to the invention can be produced by altering the composition of the starting glasses and the heat treatment thereof.

The obtained lithium disilicate-apatite glass ceramics according to the invention displayed an excellent chemical stability according to ISO test 6872 (2008). The mass loss during storage in aqueous acetic acid was less than 100 μg/cm², in particular less than 50 μg/cm².

By contrast, conventional bioactive glass ceramics show a very high mass loss and thus a very low chemical stability. They are not suitable for use as restorative dental material which repeatedly comes into contact with fluids of the most varied composition in the oral cavity.

The produced lithium disilicate-apatite glass ceramics also had a very high biaxial strength $\sigma_B$ of more than 390 and in particular of up to about 640 MPa. This strength was determined according to dental standard ISO 6872 (2008) on test pieces. The test pieces were produced by machining of the lithium metasilicate glass ceramic obtained after the 1st crystallization ($T_{K1}$) and subsequent 2nd crystallization ($T_{K2}$) to form the respective lithium disilicate-apatite glass ceramic. A CEREC®-InLab machine (Sirona, Bensheim) was used for the machining of the lithium metasilicate glass ceramic.

The lithium disilicate-apatite glass ceramics produced and the lithium metasilicate glass ceramics produced as precursor were able to be very satisfactorily brought into the form of various dental restorations by machining in a CAD/CAM process or by hot pressing, which restorations were also provided with a veneer if required. The lithium metasilicate glass ceramics proved particularly suitable for shaping by machining due to their mechanical properties.

The glass ceramics were also able to be applied by hot pressing as coatings onto in particular dental restorations, e.g. in order to veneer the latter as desired.

Finally, the glass ceramics had a linear coefficient of thermal expansion (CTE) in the broad range of from 8.6 to $11.1 \times 10^{-6} K^{-1}$ (measured in the range of from 100 to 500° C.). Specifically, materials with a CTE of less than $10 \times 10^{-6} K^{-1}$ are particularly well-suited for veneering e.g. $ZrO_2$ ceramics.

In the following table, "TMO" in the indication of the molar ratios stands for transition metal oxides.

"RT-XRD" stands for X-ray diffraction tests at room temperature.

"CTE" stands for linear coefficient of thermal expansion.

| | Example | | | | | |
|---|---|---|---|---|---|---|
| | 1 | 2 | 3 | 4 | 5 | 6 |
| $SiO_2$ | 65.3 | 64.1 | 65.3 | 63.3 | 62.1 | 72.7 |
| $GeO_2$ | — | — | — | — | 2.9 | — |
| $Li_2O$ | 13.5 | 15.0 | 13.5 | 13.3 | 13.5 | 12.1 |
| $P_2O_5$ | 5.7 | 4.5 | 5.7 | 5.2 | 4.3 | 4.3 |
| $Al_2O_3$ | 3.2 | 3.2 | 3.2 | 2.4 | 3.6 | 1.9 |
| $K_2O$ | 3.7 | 3.7 | 3.7 | — | 3.7 | 3.0 |
| $Rb_2O$ | — | — | — | 7.7 | — | — |
| $Cs_2O$ | — | — | — | — | — | — |
| CaO | 4.1 | 5.0 | 4.1 | 4.1 | 4.0 | 3.0 |
| SrO | — | — | — | — | 1.4 | — |
| F | 0.5 | 0.5 | 0.5 | 0.4 | 0.5 | 0.5 |
| $ZrO_2$ | — | — | — | — | — | — |
| $CeO_2$ | — | — | — | — | — | — |
| $La_2O_3$ | — | — | 4.0 | — | 4.0 | 2.5 |
| $Y_2O_3$ | — | — | — | 3.6 | — | — |
| $V_2O_5$ | — | — | — | — | — | — |
| $Ta_2O_5$ | — | 4.0 | — | — | — | — |
| $Nb_2O_5$ | 4.0 | — | — | — | — | — |
| $Tb_4O_7$ | — | — | — | — | — | — |
| $Er_2O_3$ | — | — | — | — | — | — |
| Σ | 100.0 | 100.0 | 100.0 | 100.0 | 100.0 | 100.0 |
| molar ratio (CaO + SrO) to TMO | 4.7 | 10.0 | 6.0 | 5.4 | 7.0 | 7.5 |
| $T_g$/° C. | 467 | 453 | 458 | 469 | 453 | 456 |
| $T_N$/° C. | 520 | 480 | 500 | 490 | 540 | 460 |
| $t_N$/min. | 20 | 40 | 10 | 40 | 10 | 30 |
| $T_{K1}$/° C. | 670 | 650 | 640 | 620 | 680 | 600 |
| $t_{K1}$/min. | 10 | 20 | 40 | 30 | 40 | 30 |
| RT-XRD after $T_{K1}$ | | | | | | |
| Main crystal phase | $Li_2SiO_3$ | $Li_2SiO_3$ | $Li_2SiO_3$ | $Li_2SiO_3$ | $Li_2Si_2O_5$ | $Li_2Si_2O_5$ |
| Further crystal phases | $Li_2Si_2O_5$, $Li_3PO_4$ | $Li_2Si_2O_5$ | $Li_3PO_4$ | — | $Li_2SiO_3$, $Li_3PO_4$, $Ca_5(PO_4)_3F$ | $Li_2SiO_3$ |
| $T_{K2}$/° C. | 800 | 800 | 760 | 800 | 820 | 810 |
| $t_{K2}$/min. | 10 | 15 | 60 | 30 | 10 | 20 |

|  | | | | | | |
|---|---|---|---|---|---|---|
| RT-XRD after $T_{K2}$ | | | | | | |
| Main crystal phase | $Li_2Si_2O_5$ | $Li_2Si_2O_5$ | $Li_2Si_2O_5$ | $Li_2Si_2O_5$ | $Li_2Si_2O_5$ | $Li_2Si_2O_5$ |
| Further crystal phases | $Li_3PO_4$, $Ca_5(PO_4)_3F$ | $Li_2SiO_3$, $Li_3PO_4$, $Ca_5(PO_4)_3F$ | $Li_3PO_4$, $Ca_5(PO_4)_3F$ | $Li_3PO_4$, $Ca_5(PO_4)_3F$ | $Li_2SiO_3$, $Li_3PO_4$, $Ca_{9.37}Sr_{0.63}(PO_4)_3F$ | $Li_3PO_4$, $Ca_5(PO_4)_3F$, $SiO_2$ |
| $CTE_{100-500°C}/10^{-6} \cdot K^{-1}$ | 10.3 | 11.2 | 10.5 | 10.5 | 11.1 | |
| $\sigma_B$/MPa | 442 | 637 | 385 | 562 | 548 | |

|  | Example | | | | | |
|---|---|---|---|---|---|---|
|  | 7 | 8 | 9 | 10 | 11 | 12 |
| $SiO_2$ | 65.3 | 54.9 | 61.5 | 65.3 | 61.8 | 59.9 |
| $GeO_2$ | — | — | — | — | — | — |
| $Li_2O$ | 13.5 | 18.2 | 12.4 | 13.5 | 17.1 | 18.7 |
| $P_2O_5$ | 5.7 | 4.8 | 4.3 | 5.7 | 4.4 | 4.4 |
| $Al_2O_3$ | 3.2 | 3.5 | 3.2 | 3.2 | 3.5 | 3.5 |
| $K_2O$ | 3.7 | 4.6 | — | 3.7 | 3.9 | 3.9 |
| $Rb_2O$ | — | — | — | — | — | — |
| $Cs_2O$ | — | — | 11.1 | — | — | — |
| CaO | 4.1 | — | 4.5 | 4.1 | 4.0 | 4.0 |
| SrO | — | 6.0 | — | — | — | — |
| F | 0.5 | 0.8 | 0.5 | 0.5 | 0.5 | 0.5 |
| $ZrO_2$ | — | — | — | — | — | — |
| $CeO_2$ | — | 1.8 | — | — | 1.7 | 1.9 |
| $La_2O_3$ | — | — | — | — | — | — |
| $Y_2O_3$ | — | 4.8 | — | 4.0 | — | 2.5 |
| $V_2O_5$ | — | — | — | — | 0.1 | 0.1 |
| $Ta_2O_5$ | 4.0 | — | 2.5 | — | — | — |
| $Nb_2O_5$ | — | — | — | — | 2.5 | — |
| $Tb_4O_7$ | — | 0.5 | — | — | 0.4 | 0.4 |
| $Er_2O_3$ | — | 0.1 | — | — | 0.1 | 0.2 |
| Σ | 100.0 | 100.0 | 100.0 | 100.0 | 100.0 | 100.0 |
| molar ratio (CaO + SrO) to TMO | 8.4 | 1.8 | 16.3 | 4.7 | 3.5 | 3.3 |
| $T_g$/°C | 465 | 441 | 466 | 461 | 447 | 443 |
| $T_N$/°C | 490 | 470 | 500 | 470 | 500 | 520 |
| $t_N$/min. | 60 | 60 | 10 | 120 | 10 | 10 |
| $T_{K1}$/°C | 600 | 700 | 630 | 580 | 650 | 620 |
| $t_{K1}$/min. | 30 | 20 | 30 | 60 | 20 | 30 |
| RT-XRD after $T_{K1}$ | | | | | | |
| Main crystal phase | $Li_2SiO_3$ | $Li_2SiO_3$ | $Li_2SiO_3$ | $Li_2SiO_3$ | $Li_2SiO_3$ | $Li_2SiO_3$ |
| Further crystal phases | $Li_2Si_2O_5$, $Li_3PO_4$ | — | $Li_2Si_2O_5$ | $Li_3PO_4$ | $Li_3PO_4$ | — |
| $T_{K2}$/°C | 770 | 840 | 840 | 790 | 800 | 800 |
| $t_{K2}$/min. | 30 | 10 | 10 | 20 | 30 | 20 |
| RT-XRD after $T_{K2}$ | | | | | | |
| Main crystal phase | $Li_2Si_2O_5$ | $Li_2SiO_3$ | $Li_2Si_2O_5$ | $Li_2Si_2O_5$ | $Li_2SiO_3$ | $Li_2SiO_3$ |
| Further crystal phases | $Li_3PO_4$, $Ca_5(PO_4)_3F$ | $Li_3PO_4$, $Sr_5(PO_4)_3F$ | $Cs_{0.809}(AlSi_5O_{12})$, $Li_2SiO_3$, $Li_3PO_4$, $Ca_5(PO_4)_3F$ | $Li_3PO_4$, $Ca_5(PO_4)_3F$ | $Li_2Si_2O_5$, $Li_3PO_4$, $Ca_5(PO_4)_3F$ | $Li_3PO_4$, $Ca_5(PO_4)_3F$ |
| $CTE_{100-500°C}/10^{-6} \cdot K^{-1}$ | 10.2 | | | 10.4 | | |
| $\sigma_B$/MPa | 419 | | | 392 | | |

|  | Example | | | | | |
|---|---|---|---|---|---|---|
|  | 13 | 14 | 15 | 16 | 17 | 18 |
| $SiO_2$ | 68.5 | 67.3 | 65.3 | 64.0 | 64.8 | 59.2 |
| $GeO_2$ | — | — | — | — | — | — |
| $Li_2O$ | 14.5 | 14.0 | 13.5 | 13.1 | 13.5 | 19.6 |
| $P_2O_5$ | 4.4 | 5.9 | 5.7 | 5.6 | 5.7 | 5.7 |
| $Al_2O_3$ | 3.5 | 3.3 | 3.2 | 3.2 | 3.2 | 3.2 |
| $K_2O$ | — | 3.8 | 3.7 | 3.6 | 3.7 | 3.7 |
| $Rb_2O$ | — | — | — | — | — | — |
| $Cs_2O$ | — | — | — | — | — | — |
| CaO | 4.0 | 4.2 | 4.1 | 8.0 | 4.1 | 4.1 |
| SrO | — | — | — | — | — | — |
| F | 0.5 | 0.5 | 0.5 | 0.5 | 1.0 | 0.5 |
| $ZrO_2$ | — | 1.0 | 4.0 | 2.0 | 4.0 | 4.0 |
| $CeO_2$ | 1.6 | — | — | — | — | — |
| $La_2O_3$ | — | — | — | — | — | — |
| $Y_2O_3$ | 2.5 | — | — | — | — | — |

-continued

| | | | | | | |
|---|---|---|---|---|---|---|
| $V_2O_5$ | — | — | — | — | — | — |
| $Ta_2O_5$ | 0.5 | — | — | — | — | — |
| $Nb_2O_5$ | — | — | — | — | — | — |
| $Tb_4O_7$ | — | — | — | — | — | — |
| $Er_2O_3$ | — | — | — | — | — | — |
| Σ | 100.0 | 100.0 | 100.0 | 100.0 | 100.0 | 100.0 |
| molar ratio (CaO + SrO) to TMO | 3.5 | 8.4 | 2.3 | 8.8 | 2.3 | 2.3 |
| $T_g/°C$ | 443 | 457 | 471 | 463 | 464 | 442 |
| $T_N/°C$ | 480 | 480 | 490 | 490 | 480 | 460 |
| $t_N$/min. | 10 | 10 | 10 | 10 | 10 | 10 |
| $T_{K1}/°C$ | 890 | — | 650 | — | — | — |
| $t_{K1}$/min. | 10 | — | 40 | — | — | — |
| RT-XRD after $T_{K1}$ | | | | | | |
| Main crystal phase | $Li_2Si_2O_5$ | | $Li_2SiO_3$ | | | |
| Further crystal phases | $Li_2O\cdot Al_2O_3\cdot 7.5SiO_2$, $Li_3PO_4$, $Ca_5(PO_4)_3F$, $SiO_2$ | | $Li_3PO_4$ | | | |
| $T_{K2}/°C$ | — | 790 | 780 | 810 | 780 | 820 |
| $t_{K2}$/min. | — | 60 | 60 | 60 | 60 | 60 |
| RT-XRD after $T_{K2}$ | | | | | | |
| Main crystal phase | — | $Li_2Si_2O_5$ | $Li_2Si_2O_5$ | $Li_2Si_2O_5$ | $Li_2Si_2O_5$ | $Li_2SiO_3$ |
| Further crystal phases | — | $Li_3PO_4$, $Ca_5(PO_4)_3F$ | $Li_3PO_4$, $Ca_5(PO_4)_3F$ | $Li_2SiO_3$, $Li_3PO_4$, $Ca_5(PO_4)_3F$ | $Li_3PO_4$, $Ca_5(PO_4)_3F$ | $Li_2Si_2O_5$, $Li_3PO_4$, $Ca_5(PO_4)_3F$ |
| $CTE_{100-500°C}/10^{-6}\cdot K^{-1}$ | | | 8.6 | | | |
| $\sigma_B$/Mpa | | | | | | |

| | Example | |
|---|---|---|
| | 19 | 20 |
| $SiO_2$ | 63.4 | 66.2 |
| $GeO_2$ | — | — |
| $Li_2O$ | 13.4 | 13.6 |
| $P_2O_5$ | 8.0 | 5.8 |
| $Al_2O_3$ | 3.1 | — |
| $K_2O$ | 3.6 | 3.7 |
| $Rb_2O$ | — | — |
| $Cs_2O$ | — | — |
| CaO | 4.0 | 4.2 |
| SrO | — | — |
| F | 0.5 | 0.5 |
| $ZrO_2$ | 4.0 | 6.0 |
| $CeO_2$ | — | — |
| $La_2O_3$ | — | — |
| $Y_2O_3$ | — | — |
| $V_2O_5$ | — | — |
| $Ta_2O_5$ | — | — |
| $Nb_2O_5$ | — | — |
| $Tb_4O_7$ | — | — |
| $Er_2O_3$ | — | — |
| Σ | 100.0 | 100.0 |
| molar ratio (CaO + SrO) to TMO | 2.1 | 1.6 |
| $T_g/°C$ | 484 | 473 |
| $T_N/°C$ | 500 | 490 |
| $t_N$/min. | 10 | 10 |
| $T_{K1}/°C$ | — | — |
| $t_{K1}$/min. | — | — |
| RT-XRD after $T_{K1}$ | | |
| Main crystal phase | | |
| Further crystal phases | | |
| $T_{K2}/°C$ | 800 | 830 |
| $t_{K2}$/min. | 40 | 60 |

-continued

| | | |
|---|---|---|
| RT-XRD after $T_{K2}$ | | |
| Main crystal phase | $Li_2Si_2O_5$ | $Li_2Si_2O_5$ |
| Further crystal phases | $Li_3PO_4$, $Ca_5(PO_4)_3F$ | $Li_3PO_4$, $Ca_5(PO_4)_3F$, $KLi_3Zr_2Si_{12}O_{30}$, $SiO_2$ |
| $CTE_{100-500°\,C}/$ $10^{-6} \cdot K^{-1}$ | | |
| $\sigma_B$/MPa | | |

The invention claimed is:

1. Lithium disilicate-apatite glass ceramic, which comprises lithium disilicate as main crystal phase and apatite as further crystal phase, and which comprises divalent oxide selected from the group of CaO, SrO and mixtures thereof and transition metal oxide selected from the group of oxides of transition metals with an atomic number from 39 to 79 and mixtures thereof, wherein the molar ratio of divalent oxide to transition metal oxide is in the range of from 1.0 to 20.0.

2. Glass ceramic according to claim 1, which comprises 52.0 to 75.0 wt.-% $SiO_2$.

3. Glass ceramic according to claim 1, which comprises 10.0 to 20.0 wt.-% $Li_2O$.

4. Glass ceramic according to claim 1, which comprises 4.0 to 8.0 wt.-% $P_2O_5$.

5. Glass ceramic according to claim 1, which comprises 2.0 to 9.0 wt.-% divalent oxide.

6. Glass ceramic according to claim 1, which comprises 2.5 to 8.5 wt.-% CaO.

7. Glass ceramic according to claim 1, which comprises 1.0 to 6.5 wt.-% SrO.

8. Glass ceramic according to claim 1, which comprises 0.1 to 1.5 wt.-% F.

9. Glass ceramic according to claim 1, which comprises 0 to 4.0 wt.-% $Al_2O_3$.

10. Glass ceramic according to claim 1, which comprises 0.5 to 8.5 wt.-% transition metal oxide.

11. Glass ceramic according to claim 1, in which the transition metal oxide is selected from the group of $La_2O_3$, $Y_2O_3$, $Er_2O_3$, $ZrO_2$, $CeO_2$, $Tb_4O_7$, $V_2O_5$, $Ta_2O_5$, $Nb_2O_5$ and mixtures thereof.

12. Glass ceramic according to claim 1, in which the transition metal oxide is present
according to the formula $Me_2O_3$ in an amount of from 0 to 5.0 wt.-%,
according to the formula $MeO_2$ in an amount of from 0 to 6.5 wt.-%,
according to the formula $Me_4O_7$ in an amount of from 0 to 1.0 wt.-% and/or
according to the formula $Me_2O_5$ in an amount of from 0 to 5.0 wt.-%.

13. Glass ceramic according to claim 1, which comprises monovalent oxide selected from the group of $Na_2O$, $K_2O$, $Rb_2O$, $Cs_2O$ and mixtures thereof in an amount of from 0 to 12.0 wt.-%.

14. Glass ceramic according to claim 1, which comprises fluoroapatite as apatite.

15. Glass ceramic according to claim 1, in which the apatite crystal phase makes up 0.5 to 10 wt.-% of the glass ceramic and/or the apatite crystals have an average size of from 5 to 500 nm.

16. Lithium metasilicate-apatite glass ceramic, which comprises lithium metasilicate as main crystal phase and apatite as further crystal phase, and which comprises divalent oxide selected from the group of CaO, SrO and mixtures thereof and transition metal oxide selected from the group of oxides of transition metals with an atomic number from 39 to 79 and mixtures thereof, wherein the molar ratio of divalent oxide to transition metal oxide is in the range of from 1.0 to 20.0.

17. Glass ceramic according to claim 1, wherein the glass ceramicis present in the form of a powder, a granulate, a blank or a dental restoration.

18. Process for the preparation of the glass ceramic according to claim 1, wherein a starting glass or a lithium metasilicate glass ceramic is subjected to at least one heat treatment in the range of from 450° to 1000° C.

19. Process according to claim 18, wherein
(a) the starting glass is subjected to a heat treatment at a temperature of from 450 to 600° C. in order to form starting glass with nuclei, and
(b) the starting glass with nuclei is subjected to a heat treatment at a temperature of from 700 to 1000° C. in order to form the lithium disilicate-apatite glass ceramic.

20. Process of using the lithium disilicate-apatite glass ceramic according to claim 1 as dental material for coating dental restorations or for the preparation of dental restorations.

21. Process of using the lithium disilicate-apatite glass ceramic according to claim 20, wherein the lithium disilicate-apatite glass ceramic is given, by pressing or machining, a shape of the dental restoration, as a bridge, inlay, onlay, veneer, abutment, partial crown, crown or facet.

22. Lithium disilicate-apatite glass ceramic, according to claim 1, wherein the molar ratio of divalent oxide to transition metal oxide is in the range of from 1.0 to 17.0.

23. Lithium disilicate-apatite glass ceramic, according to claim 1, wherein the molar ratio of divalent oxide to transition metal oxide is in the range of from 1.5 to 16.5.

24. Glass ceramic according to claim 2, which comprises 54.0 to 73.0 wt.-% $SiO_2$.

25. Glass ceramic according to claim 3, which comprises 2.0 to 20.0 wt.-% $Li_2O$.

26. Glass ceramic according to claim 5, which comprises 3.0 to 8.0 wt.-% divalent oxide.

27. Glass ceramic according to claim 6, which comprises 3.0 to 8.0 wt.-% CaO.

28. Glass ceramic according to claim 7, which comprises 1.0 to 6.0 wt.-% SrO.

29. Glass ceramic according claim 8, which comprises 0.3 to 1.0 wt.-% F.

30. Glass ceramic according to claim 9, which comprises 1.0 to 4.0 $Al_2O_3$.

31. Glass ceramic according to claim 9, which comprises 1.5 to 4.0 wt.-% $Al_2O_3$.

32. Glass ceramic according to claim 10, which comprises 1.0 to 8.0 wt.-% transition metal oxide.

33. Glass ceramic according to claim 10, which comprises 2.0 to 7.5 wt.-% transition metal oxide.

34. Glass ceramic according to claim 12, in which the transition metal oxide is present
  according to the formula $Me_2O_3$ in an amount of from 2.5 to 4.0 wt.-%,
  according to the formula $MeO_2$ in an amount of from 1.0 to 6.0 wt.-%,
  according to the formula $Me_4O_7$ in an amount of from 0.4 to 1.0 wt.-% and/or
  according to the formula $Me_2O_5$ in an amount of from 0.1 to 4.0 wt.-%.

35. Glass ceramic according to claim 13, which comprises monovalent oxide selected from the group of $Na_2O$, $K_2O$, $Rb_2O$, $Cs_2O$ and mixtures thereof in an amount of from 0 to 12.0 wt.-%.

36. Glass ceramic according to claim 13, which comprises monovalent oxide selected from the group of $Na_2O$, $K_2O$, $Rb_2O$, $Cs_2O$ and mixtures thereof in an amount of from 3.0 to 11.5 wt.-%.

37. Glass ceramic according to claim 15, in which the apatite crystal phase makes up 1 to 10 and preferably 2 to 8 wt.-% of the glass ceramic and/or the apatite crystals have an average size of from 10 to 300.

38. Glass ceramic according to claim 15, in which the apatite crystal phase makes up 2 to 8 wt.-% of the glass ceramic and/or the apatite crystals have an average size of 20 to 200 nm.

39. Lithium metasilicate glass ceramic according to claim 16, wherein the lithium metasilicate glass ceramic is present in the form of a powder, a granulate, a blank or a dental restoration.

40. Process of using the lithium metasilicate glass ceramic according to claim 16 as dental material for coating dental restorations or for the preparation of dental restorations.

41. Process of using the lithium metasilicate glass ceramic according to claim 40, wherein the lithium metasilicate glass ceramic is given, by pressing or machining, a shape of the dental restoration as a bridge, inlay, onlay, veneer, abutment, partial crown, crown or facet.

* * * * *